US011259880B1

(12) United States Patent
Geist

(10) Patent No.: US 11,259,880 B1
(45) Date of Patent: Mar. 1, 2022

(54) GUIDING THE TRAJECTORY OF A SECOND SURGICAL DEVICE

(71) Applicant: INTEGRITY IMPLANTS INC., Palm Beach Gardens, FL (US)

(72) Inventor: Wyatt Geist, Jupiter, FL (US)

(73) Assignee: INTEGRITY IMPLANTS INC., Palm Beach Gardens, FL (US)

( * ) Notice: Subject to any disclaimer, the term of this patent is extended or adjusted under 35 U.S.C. 154(b) by 286 days.

(21) Appl. No.: 16/258,529

(22) Filed: Jan. 25, 2019

Related U.S. Application Data

(60) Provisional application No. 62/622,088, filed on Jan. 25, 2018.

(51) Int. Cl.
*A61B 17/17* (2006.01)
*A61B 34/20* (2016.01)
*A61B 34/10* (2016.01)
*A61B 90/00* (2016.01)
*A61B 17/16* (2006.01)

(52) U.S. Cl.
CPC .............. *A61B 34/20* (2016.02); *A61B 17/17* (2013.01); *A61B 34/10* (2016.02); *A61B 90/37* (2016.02); *A61B 17/1671* (2013.01); *A61B 17/1757* (2013.01); *A61B 2034/107* (2016.02); *A61B 2034/2046* (2016.02)

(58) Field of Classification Search
CPC ..... A61B 34/20; A61B 34/10; A61B 17/1671; A61B 17/17
See application file for complete search history.

(56) References Cited

U.S. PATENT DOCUMENTS

| 6,428,547 B1 | 8/2002 | Vilsmeier et al. |
| 7,951,153 B2* | 5/2011 | Abdou ................. A61F 2/4611 606/99 |
| 8,617,176 B2* | 12/2013 | Lizardi .............. A61B 17/1714 606/98 |
| 10,687,845 B2 | 6/2020 | Geist |
| 2006/0079908 A1* | 4/2006 | Lieberman ......... A61B 17/1757 606/99 |
| 2006/0085072 A1 | 4/2006 | Funk et al. |
| 2006/0217731 A1 | 9/2006 | Gil et al. |
| 2008/0243249 A1* | 10/2008 | Kohm ................. A61B 17/149 623/17.12 |

(Continued)

FOREIGN PATENT DOCUMENTS

| DE | 3205404 | 9/1983 |
| EP | 0923906 A2 | 6/1999 |

(Continued)

OTHER PUBLICATIONS

U.S. Appl. No. 62/002,734, filed May 23, 2014, Geist—owned by Applicant.

(Continued)

*Primary Examiner* — Christian A Sevilla
(74) *Attorney, Agent, or Firm* — Brian S. Boyer; Syndicated Law, PC

(57) ABSTRACT

Systems and methods are provided for trajectory guidance during surgical procedures, for example, monitoring and identifying a desired trajectory of surgical access devices and implants for the purpose of preventing unintended injury to surrounding tissues, such as nerves, blood vessels, cartilage, or bone.

22 Claims, 7 Drawing Sheets

(56) References Cited

U.S. PATENT DOCUMENTS

| | | | |
|---|---|---|---|
| 2010/0324560 A1* | 12/2010 | Suda | A61B 17/1757 606/79 |
| 2012/0078252 A1 | 3/2012 | Huebner et al. | |
| 2012/0226301 A1 | 9/2012 | Geist | |
| 2012/0253353 A1* | 10/2012 | McBride | A61B 17/1757 606/97 |
| 2013/0208202 A1 | 8/2013 | Nakanishi et al. | |
| 2020/0268409 A1 | 8/2020 | Geist | |

FOREIGN PATENT DOCUMENTS

| | | |
|---|---|---|
| JP | 2007-105392 | 4/2007 |
| JP | 2009-261485 A | 11/2009 |
| JP | 2013-529120 A | 12/2011 |
| WO | WO 2009/055034 | 4/2009 |
| WO | WO 2013/180191 | 12/2013 |
| WO | WO 2014/005225 | 1/2014 |

OTHER PUBLICATIONS

U.S. Appl. No. 62/059,455, filed Oct. 3, 2014, Geist—owned by Applicant.
U.S. Appl. No. 62/622,088, filed Jan. 25, 2018, Geist—owned by Applicant.
PCT/US2015/032235 Published as WO 2015/183747, Geist—owned by Applicant, Dec. 3, 2015.
Written opinion and search report for PCT/US2015/032235, Geist—owned by Applicant, dated Dec. 3, 2015.
European search report for 15790705.6, dated Mar. 29, 2017, Geist—owned by Applicant.
Marksman Targeting [online] URL: http://www.marksmantargeting.com [retrieved on Oct. 22, 2020].

* cited by examiner

GUIDING THE TRAJECTORY OF A SECOND SURGICAL DEVICE

CROSS-REFERENCE TO RELATED APPLICATIONS

This application claims priority to U.S. Provisional Application No. 62/622,088, filed Jan. 25, 2018, which is hereby incorporated herein by reference in it's entirety.

BACKGROUND

Field of the Invention

The present disclosure relates generally to surgical systems and methods, and more particularly to systems and methods for guiding the trajectory of a surgical device during surgical procedures.

Description of Related Art

Medical procedures involving the vertebrae are normally complicated because of the preciseness and accuracy required to avoid both neural damage and injury to major blood vessels. Precision depth guided instruments are required to perform percutaneous spinal surgery. These surgeries sometimes require penetration of the hard cortical bone of the vertebra and traversal of the softer cancellous bone lying thereunder. A large force is normally required by the surgeon to penetrate the cortical bone. Once the cortical bone is penetrated, extreme care must then be taken to avoid rapidly penetrating through all of the cancellous bone. There is also the danger of rapidly passing through the cancellous bone and then through the cortical bone on the other side of the vertebra. This can result in injury or damage to the spinal cord and/or other organs or blood vessels located adjacent the spine. In some instances, the force required to penetrate the cortical bone is greater than a surgeon can apply by hand. In these instances, a hammer or other similar instrument is required to force the instrument through the cortical bone. When a hammer or similar instrument is used, there is a greater danger of the instrument passing rapidly through the cancellous bone and out the other side of the vertebra.

In many instances during a minimally invasive spine surgery, for example a TLIF procedure, a single incision is used for multiple steps, including but not limited to accessing and cleaning a disc space, inserting an implant into the disc space, and placing bone anchors (e.g. pedicle screws). This technique is useful but not without disadvantages, including but not limited to tissue disruption, and approach angle into disc space being problematic for larger implants.

For at least the above reasons, one of skill will appreciate having systems and methods for monitoring and identifying a desired trajectory of surgical access devices and implants for the purpose of preventing unintended injury to surrounding tissues, such as nerves, blood vessels, cartilage, or bone. The systems and methods provided herein, for example, allow the surgeon to set the trajectory of a surgical access device, with precision and accuracy, before ever cutting a subject's skin. Moreover, due to the safety advantages of the use of Kambin's Triangle in accessing tissue during a spinal surgery, one of skill will particularly appreciate the surprisingly effective ability of the systems and methods provided herein to set a trajectory for access to Kambin's Triangle before ever cutting the skin of the subject at this desirable access point.

SUMMARY

Systems and methods for trajectory guidance during surgical procedures are provided herein. For example, systems and methods are provided for monitoring and identifying a desired trajectory of surgical access devices and implants for the purpose of preventing unintended injury to surrounding tissues, such as nerves, blood vessels, cartilage, or bone.

Methods of setting a trajectory angle for access by a second surgical device into a subject by referencing a first surgical device are provided, for example. In some embodiments, the methods can include implanting a portion of the reference surgical device in the subject to set a reference trajectory angle, which is a first direction of angulation and a first angle of first access into a subject, wherein the reference trajectory angle is formed by the central axis of the implanted portion of the reference surgical device; and, establishing the trajectory angle for access by the second surgical device which is a second direction of angulation and a second angle of second access into the subject, using the central axis of the implanted portion of the first surgical device forming a reference point of origin, the establishing including measuring the trajectory angle from the reference point of origin.

In some embodiments, the measuring includes obtaining a trajectory guidance device operable for attaching to the reference surgical device. And, in some embodiments, the reference surgical device has an implanted portion, also referred to as an access portion, and a structural portion having a central axis, and the measuring includes obtaining a trajectory guidance device adapted for attaching to the structural portion of the reference surgical device. In some embodiments, the trajectory guidance device can have a guidance portion with a first rotatable axis concentric, or near concentric, with the central axis of the structural portion of the reference surgical device when attached; and, an angle scale portion for determining the trajectory angle for access by the second surgical device.

One of skill will appreciate that the reference surgical device can be any point of reference used surgically to establish a point of origin for setting the trajectory of access for the second surgical device. For example, the reference surgical device is a pin, a needle, a rod, a screw, or a combination thereof. In some embodiments, the reference surgical device is a trephine. And, in some embodiments, the reference surgical device is a Jamshidi needle. In some embodiments, the second surgical device is a dilator. And, in some embodiments, the second surgical device is a catheter.

One of skill will appreciate the value of the systems and methods in spinal surgeries. In some embodiments, the first surgical device can be implanted into a vertebral pedicle at the reference trajectory angle, and the trajectory angle for access by the second surgical device second surgical device can be established for access into the Kambin's Triangle adjacent to the vertebral pedicle.

One of skill will also appreciate having the systems and methods provided herein in the form of a kit for ease of access and use. In some embodiments, a kit for performing a spinal surgery on a subject is provided and includes a first surgical device having an access portion and a structural portion having a central axis; a second surgical device having an access portion with a central axis; and, a trajectory guidance device adapted for operably connecting with the structural portion of the first surgical device and having an angle measurement component, such as the angle scale portion, to establish the trajectory of access into the subject by the access portion of the second surgical device. In some embodiments, the first surgical device is a trephine, the second surgical device is a dilator, and the trajectory guidance device has a guidance portion with a first rotatable axis concentric, or near concentric, with the central axis of the structural portion of the first surgical device when attached; and, an angle scale portion for determining the trajectory angle of the access portion of the second device for the access into the subject.

BRIEF DESCRIPTION OF THE DRAWINGS

Many advantages of the present disclosure will be apparent to those skilled in the art with a reading of this specification in conjunction with the attached drawings, wherein like reference numerals are applied to like elements and wherein.

DETAILED DESCRIPTION

Figure 1:
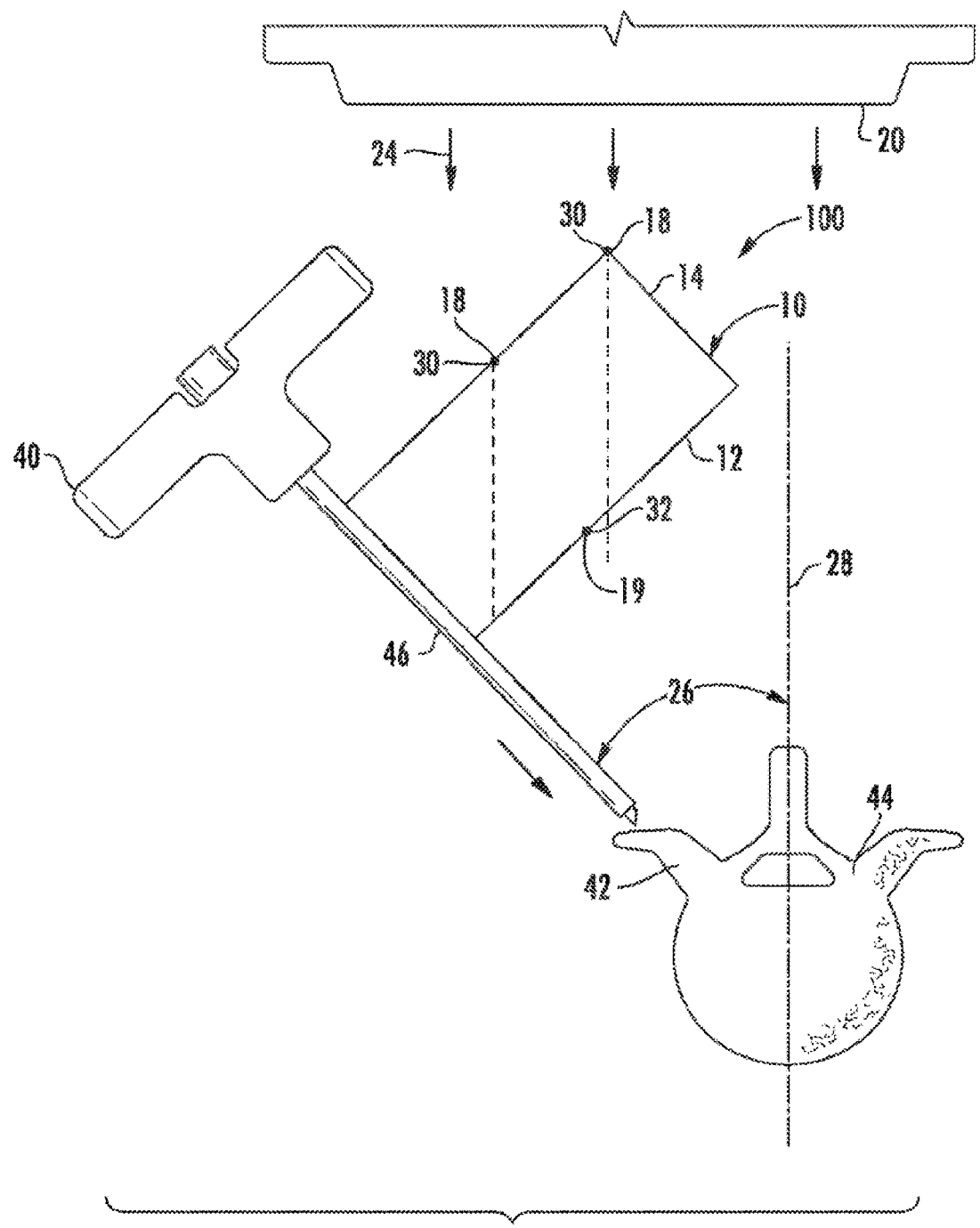
FIG. 1 is a side view of one example embodiment of a trajectory guidance instrument, illustrated with a Jamshidi needle and a partial view of a C-arm type x-ray device, according to some embodiments.

Systems and methods for trajectory guidance during surgical procedures are provided herein. For example, systems and methods are provided for monitoring and identifying a desired trajectory of surgical access devices and implants for at least the purpose of preventing, or at least avoiding or mitigating the risk of, an unintended injury to surrounding tissues, such as nerves, blood vessels, cartilage, or bone.

Methods of setting a trajectory angle for access by a second surgical device into a subject by referencing a first surgical device are provided, for example. In some embodiments, such methods can include implanting a portion of the reference surgical device in the subject to set a reference trajectory angle, which is a first direction of angulation and a first angle of first access into a subject, wherein the reference angle is formed by the central axis of the implanted portion of the reference surgical device; and, establishing the trajectory angle for access by the second surgical device using the central axis of the implanted portion forming a reference point of origin, which is a second direction of angulation and a second angle of second access into the subject, the establishing including measuring the trajectory angle from the reference point of origin.

In some embodiments, the measuring includes obtaining a trajectory guidance device operable for attaching to the reference surgical device. And, in some embodiments, the reference surgical device has an implanted portion and a structural portion having a central axis, and the measuring includes obtaining a trajectory guidance device adapted for attaching to the structural portion of the reference surgical device. In some embodiments, the trajectory guidance device can have a guidance portion with a first rotatable axis concentric, or near concentric, with the central axis of the structural portion of the reference surgical device when attached; and, an angle scale portion for determining the trajectory angle for access by the second surgical device.

One of skill will appreciate that the reference surgical device can be any point of reference used surgically to establish a point of origin for setting the trajectory of access for the second surgical device. For example, the reference surgical device is a pin, a needle, a rod, a screw, or a combination thereof. In some embodiments, the reference surgical device is a trephine. And, in some embodiments, the reference surgical device is a Jamshidi needle. In some embodiments, the second surgical device is a dilator. And, in some embodiments, the second surgical device is a catheter. The surgical instrument can be a cutting instrument or a dissecting instrument, a grasping instrument or a holding instrument, a hemostatic instrument, a retraction instrument, or a tissue-unifying instrument. Accordingly, one of skill will appreciate that the "functional portion" of the surgical instrument will include the portion of the surgical device that may be configured to do the "function", which can be, for example, the cutting or dissecting, the grasping or holding, the retracting, the tissue-unifying, the preventing of the flow of blood, or a combination thereof.

The term "animal" can be used interchangeably, in some embodiments, with the terms "subject" and "patient". Such terms can be used to refer to an animal such as a mammal including, but not limited to, non-primates such as, for example, a cow, pig, horse, cat, dog, rat and mouse; and primates such as, for example, a monkey or a human. As such, the terms "subject" and "patient" can also be applied to non-human biologic applications including, but not limited to, veterinary, companion animals, commercial livestock, and the like. Moreover, "tissue" can be used to refer, for example, to epithelial tissue, connective tissue, muscle tissue and/or nerve tissue, in some embodiments. One of skill will appreciate that epithelial tissues form the surface of the skin, and line many cavities of the body and covers the internal organs; connective tissue includes cartilage, bone, adipose, and blood, of which cartilage and bone are of particular focus herein; muscle tissue includes skeletal, smooth, and cardiac muscle; and the neural tissues include neurons that process and transfer information throughout a subject's body. The tissue of interest in the surgical procedure can include, for example, intervertebral tissue and cortical portion of a vertebral endplate, in some embodiments. The functional portion of the surgical instrument can be configured, for example, to remove the intervertebral tissue.

One of skill will appreciate the value of the systems and methods in spinal surgeries. In some embodiments, the first surgical device can be implanted into a vertebral pedicle at the reference trajectory angle, and the trajectory angle for access by the second surgical device second surgical device can be established for access into the Kambin's Triangle adjacent to the vertebral pedicle.

One of skill will also appreciate having the systems and methods provided herein in the form of a kit for ease of access and use. In some embodiments, a kit for performing a spinal surgery on a subject is provided and includes a first surgical device having an access portion and a structural portion having a central axis; a second surgical device having an access portion with a central axis; and, a trajectory guidance device adapted for operably connecting with the structural portion of the first surgical device and having an angle measurement component, such as the angle scale portion, to establish the trajectory of access into the subject by the access portion of the second surgical device. In some embodiments, the first surgical device is a trephine, the second surgical device is a dilator, and the trajectory guidance device has a guidance portion with a first rotatable axis concentric, or near concentric, with the central axis of the structural portion of the first surgical device when attached; and, an angle scale portion for determining the trajectory angle of the access portion of the second device for the access into the subject.

One of skill will appreciate that the systems and methods can include steps set-forth in greater detail. In some embodiments, a method of setting a surgical trajectory for access by a second surgical device using the fixed angle of a first surgical device in a subject can include, for example, obtaining a trajectory guidance device for a first surgical device and a second surgical device, the first surgical device and the second surgical device each having an access portion with a tip and a central axis concentric with the tip. The trajectory device can have a guidance portion with a first rotatable axis concentric, or near concentric, with the central axis of the access portion of the first surgical device when in operable connection with the first surgical device; and, a linear angle scale portion having a central axis at an angle, $\theta_1$, from the first rotatable axis. The trajectory guidance device can be adapted for attaching to the first surgical device.

It should be appreciated that any surgical device can be used in the methods set-forth herein, and one of skill will appreciate that the selection of device depends on the function needed, which is determined by the surgical procedure of interest. In some embodiments, the surgical device is a pin, a needle, a rod, a screw, or a combination thereof. And, in some embodiments, the surgical device can be a dilator or catheter. In some embodiments, the surgical device can be designed for cutting and dissecting, clamping and occluding, retracting and exposing, grasping and holding, or dilating and/or providing passage for another surgical instrument. Surgical instruments designed for single port surgery can be used, for example. An example of a surgical instrument that can be used in a spinal procedure, such as a spinal fusion procedure, is a trephine, such as a Jamshidi needle, and the trephine can have a handle which can be adapted, for example, to accept the trajectory guidance system, or serve as the trajectory guidance system, such as those taught herein.

In some embodiments, the methods include placing the guidance portion of the trajectory device in operable connection with the first surgical device. The methods also can include obtaining a radiograph to help establish points of reference for the angulation of the surgical devices. For example, a radiograph of a target site within the subject can be obtained, the target site centered at or near the center of the radiograph, and the obtaining of the radiograph including directing the axis of the central beam of a source of radiation for the radiograph at or near the center of the target site. It should be appreciated that other imaging techniques can be used with the systems and methods taught herein. An example of an alternative imaging system is ultrasound. Another examiner of an alternative imaging system is MRI (magnetic resonance imaging). The trajectory guidance system can be marked for use with the imaging system of choice. For example, an x-ray imaging system could be used with a trajectory guidance system that has radio-opaque markings to show angle measurements, and these markings can be placed in an at least substantially radiolucent support material for visualization on the radiograph. Such markings can be used alone or "stacked", such that markings intended to represent the same angle, on the top and on the bottom of the guidance system, are superimposed when in alignment, or are separated when the markings are not aligned. Stacked markings can aid in determining if the established trajectory is potentially incorrect due to the positioning of the source of the x-ray, for example.

In some embodiments, the methods include establishing a start position of the first surgical device on the subject. Establishing the start position can include, for example, placing the tip of the access portion of the first surgical device on the subject at a first point of entry for a first access that is at or near the center of the radiograph; and, orienting the central axis of the access portion of the first surgical device concentric or near concentric with the central beam of the source of radiation as a starting position for the first surgical device on the angle scale portion. The method can include establishing a first direction of angulation and a first angle of the first access into the subject, the establishing including selecting the first direction of angulation and the first angle for a first pivoting the central axis of the access portion relative to the central axis of the central beam. The method can also include aligning the central axis of the linear angle scale with the first direction of angulation for the first pivoting; and, while immobilizing the tip of the access portion of the first surgical device at the first point of entry, performing the first pivoting of the central axis of the access portion of the first surgical device in the first direction until the first angle for pivoting is reached on the linear angle scale. Fixing the first surgical device, the reference surgical device, at the first angle allows for use of the first surgical device as a reference point, in some embodiments. The fixing of the first surgical device at the first angle can include initiating the first access into the subject at the first point of entry and penetrating the tip of the first surgical device to a first depth into the subject that corresponds to a calibration of the first angle on the linear angle scale.

It should be appreciated that the depth of the first access, or first depth, is the depth of the tip of the first surgical device and establishes the point of angulation for the trajectory guidance device. Since the first angle is fixed, the method can include establishing the second direction of angulation and the second angle of the second access into the subject. It should be appreciated that the second direction of angulation and the second angle originates from the tip of the first surgical device. As such, the establishing can include selecting the second direction of angulation and the second angle for the central axis of the access portion of the second surgical device relative to the central axis of the access portion of the first surgical device; aligning the central axis of the linear angle scale with the second direction of angulation; and, while immobilizing the tip of the access portion of the second surgical device at the second point of entry, performing a second pivoting of the central axis of the access portion of the second surgical device in the second direction until the second angle is reached on the linear angle scale.

As with the first surgical device, the second surgical device can be fixed. In some embodiments, the fixing of the second surgical device at the second angle is included, and the fixing includes initiating the second access into the subject at the second point of entry and penetrating the tip of the second surgical device to a second depth into the subject that corresponds to a calibration of the second angle on the linear angle scale.

As noted above, the systems and methods provided herein are especially useful in spinal procedures, for example, such as spinal fusion procedures. In some embodiments, the target site is a vertebral pedicle, the first access is into the vertebral pedicle of the subject, and the second access is into the Kambin's Triangle adjacent to the vertebral pedicle. The first surgical device can be a pin, a needle, a rod, a screw, or a combination thereof; a trephine, perhaps a Jamshidi needle; a dilator and/or perhaps a catheter. One of skill will appreciate that the surgical devices that can be used are numerous and not limited to the above.

It should also be appreciated that a number of operable connections can be designed for attaching the trajectory guidance device to the first surgical device, wherein the angle, $\theta_1$, of the central axis of the linear angle scale portion from the first rotatable axis of the guidance portion of the linear angle scale ranges from about 45° to about 135°, and can be any amount or range therein in increments of 1°. And, in some embodiments, the angle scale is not linear but, rather curved like a protractor. In some embodiments, the angle, $\theta_1$, is about 50°, about 55°, about 60°, about 65°, about 70°, about 75°, about 80°, about 85°, about 90°, about 95°, about 100°, about 105°, about 110°, about 115°, about 120°, about 125°, about 130°, or any amount or range therein in increments of 1°.

In should also be appreciated that the trajectory guidance device can be integral with the first surgical device, such that the guidance device is part of the surgical device itself. However, it should also be appreciated that, whether integral or not, the trajectory guidance device can also be configured to rotate around the access portion of the first surgical device.

The embodiments and surgical uses of a trajectory guidance system described herein can be used to enhance the safety and efficiency of surgical procedures, as well as avoid and/or mitigate the risk of injury during a surgical procedure. In some embodiments, the systems and methods provided herein may facilitate safe and reproducible pedicle screw placement by monitoring the axial trajectory of various surgical instruments used during pilot hole formation and/or screw insertion.

In some embodiments, intraoperative imaging performance may be improved and radiation exposure minimized by monitoring the precise orientation of the imaging device. For example, a robotic system is provided, wherein the systems can include a robotic arm for manipulation of the first surgical device to a first desired angle, and establishing the angle and access of the second surgical device with little to no exposure of a medical professional to radiation. In some embodiments, the robotic system can include any control input device for controlling the manipulation of the robotic arm. An example of such a control device is a joystick. An augmented system can include enhanced graphical user interfaces including, for example, a head-mounted display, such as a virtual reality headset and/or simply a large screen that is magnified for an enhanced graphical user interface. Such robotic systems can be equipped with a sensitive tactile feedback for enhanced control.

In particular, however, a method of using the systems and methods taught herein can be controlled to prepare an intervertebral disc for a spinal fusion procedure. Such a method might include, for example, creating a point of entry into an intervertebral disc, the intervertebral disc having a nucleus pulposus surrounded by an annulus fibrosis; and, removing the intervertebral tissue from within the intervertebral space, the intervertebral space having a top vertebral plate and a bottom vertebral plate while preserving the annulus fibrosis.

In some embodiments, the method can be part of a spinal fusion procedure that uses a scaffolding to support fusion of an intervertebral disc space, such that the method can further include inserting a scaffolding through the point of entry into the intervertebral space; and, adding a grafting material to the intervertebral space for the fusion.

Such systems and methods can be computerized, and even robotic. One of skill will understand that the methods and systems provided herein can include hardware and software, in some embodiments, the combination of which can a "computer", for example, having a processor and memory. It should also be understood that the technology provided herein also includes "software", which can include instructions for execution of function by the processor, the software including, for example, a set of modules, engines, and instructions for executing the modules and/or engines by the processor. As such, in some embodiments, the system can further include an input module on a non-transitory computer readable storage medium. The input module can, for example, receive input from an "operator". The operator input can be used in identifying, for example, any surgical parameters of interest to a particular surgical procedure.

Robotics can increase safety and efficiency in techniques that require precision. However robotics may be used throughout the surgical procedure to increase safety and efficiency to several aspects. For example, one such aspect is determining an approach trajectory and establishing an operative corridor to a surgical target site (e.g. an intervertebral disc space). In most cases, this aspect is performed manually by a surgeon who never leaves the X-ray field even though numerous (and in some instances, continuous) radiation exposure events may happen during the procedure. This is especially hazardous for high-volume surgeons. In the current example, one or more surgical needles (e.g. Jamshidi needles) may be attached to the distal end(s) of one or more robotic arms controlled by a computer system. The surgeon can be out of the X-Ray field entirely, or at least substantially, without giving up the ability to control the positioning of the surgical needle while the medial-lateral approach angle is determined. The robotically-positioned needle(s) may then be verified using additional targeting devices/techniques. Once established, the robotic arm may then continue to hold the surgical needle (and subsequent dilators, retractors, etc.) in place to establish and maintain an operative corridor (e.g. minimally invasive, percutaneous, and/or open). The term "substantially" can be used to refer to an amount that is appreciable to the skilled artisan. In some embodiments, a surgeon is out of an x-ray field substantially when the radiation exposure is reduced by at least about 10%, about 20%, about 30%, about 40%, about 50%, about 60%, about 70%, about 80%, about 90%, or any amount or range therein in amounts of 1%.

As such, in some embodiments, the systems and methods can include a surgical device having a functional portion, and a robotic arm configured for holding the surgical instrument and contacting the functional portion of the surgical instrument with an animal tissue. Likewise, the systems and methods can include a computer having a processor; and, a memory, wherein the memory can be configured to include, for example, a trajectory module on a non-transitory computer readable storage medium. The trajectory module can be configured such that it is operable to instruct the processor to alter the trajectory of the access of a surgical device using the robotic arm.

It is important to note that even though the various method steps disclosed herein can be driven by robotics, they are not necessarily occurring unsupervised, but rather trained surgeons and/or technicians can be nearby monitoring and controlling the data collection and operation of the robotics instrument. One advantage of using robotics to control the precision movements of the procedure is that the surgeons and/or technicians can be out of the X-Ray field and still have the ability to monitor and/or control the action of the robotics.

One of skill will appreciate that monitoring the orientation of surgical access instruments can aid in both the insertion and positioning of the access instruments themselves, as well as aiding in the later insertion of instruments and/or implants through or with the surgical access instruments. In some embodiments, the trajectory guidance system may be used to measure multiple trajectory angles after placement of an initial surgical instrument. It should be appreciated that the systems and methods provided herein may be suitable for use in any number of additional surgical actions where the angular orientation or trajectory or depth (linear distance traveled) of instrumentation and/or implants is desired. In some embodiments, for example, the systems and methods provided herein may be useful in directing, among other things, the formation of tunnels for ligament or tendon repair and the placement of facet screws. Other uses may include orientation of drills, saws, cutters or other hand operated tools used in the performance of surgery where specific fiducial markers may be useful.

Figure 2:
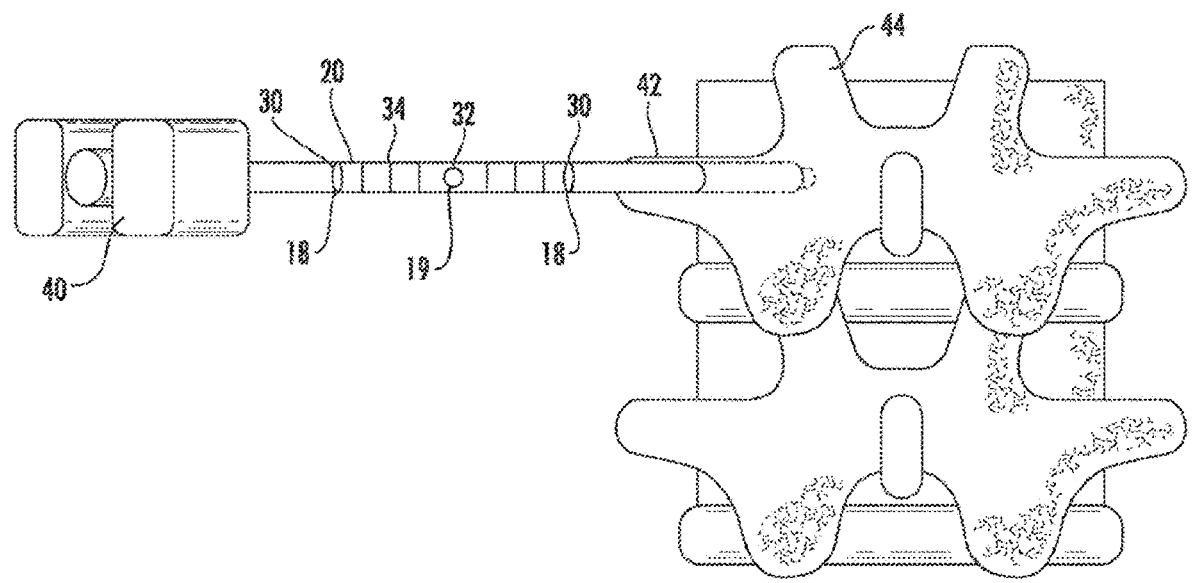
FIG. 2 is a top view of the trajectory guidance instrument of FIG. 1, according to some embodiments.
Figure 3:
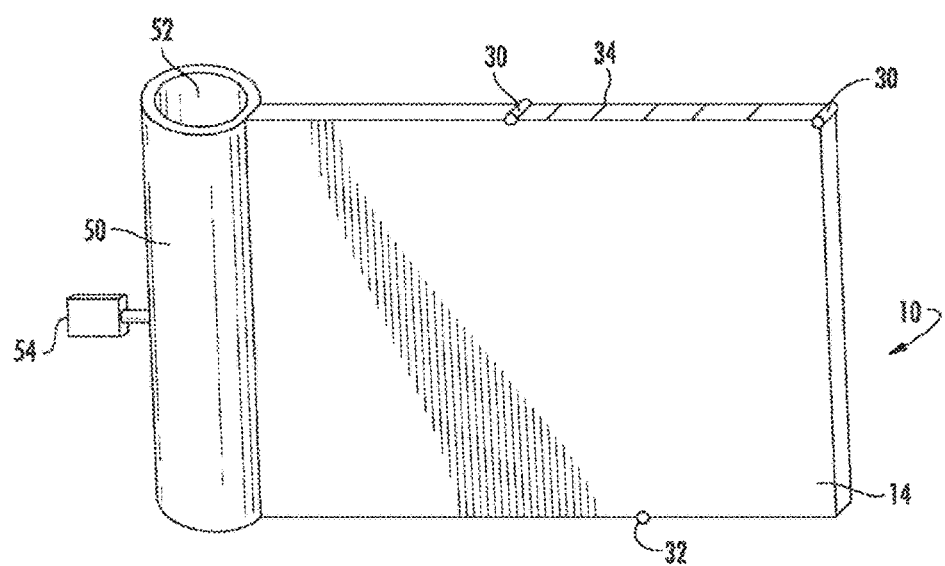
FIG. 3 is a perspective view of one example of an outrigger forming part of the trajectory guidance instrument of FIG. 1, according to some embodiments.

FIGS. 1-2 illustrate one example embodiment of the present disclosure and one manner in which it may be assembled, according to some embodiments. The example shown in FIGS. 1-2 is similar to that shown and described in commonly-owned PCT Patent Application Serial number PCT/US15/32235, filed 22 May 2015 and entitled "Trajectory Guidance Device and System for Surgical Instruments," the entire contents of which are incorporated by reference into this disclosure as if set forth fully herein. Note that identical reference numerals refer to like components in the various figures. FIG. 1 is a schematic representation showing an embodiment of a precision trajectory guidance instrument 100, illustrated herein as an outrigger 10, secured to a structural portion of a first surgical device, such as a Jamshidi needle 40. The outrigger 10 comprises a radiolucent body portion 14 having radiopaque indicia 18 forming a front sight 30 and a rear sight 32 which can be aligned under radiography for the purpose of preventing unintended injury to surrounding tissues, nerves, blood vessels, cartilage or bone. The visibility of the indicia 18 under radiography ensures a precise trajectory and/or monitoring of the trajectory of surgical instruments and/or implants in any number of surgical procedures, such as bone marrow biopsies, placement of spinal implants, spinal surgery, including ensuring proper placement of pedicle screws during pedicle fixation procedures, and ensuring proper trajectory during the establishment of an operative corridor to a spinal target site. A trajectory indicium 19, e.g. rear sight 32, which is also radiopaque is provided for determining an angular relationship and is aligned in a horizontal or vertical plane between the front sights 30. The indicia 18 can also include at least one reference trajectory sight 34, which indicates various degree graduations between the front sights 30 that form an angle scale portion as shown in FIGS. 2 and 3 between front sights 30. In some embodiments, the indicia 18 may be embossed, printed, painted, embedded or otherwise imprinted on a sticker, clip or outrigger. The radiopaque materials utilized for the indicia may include one of several metals known to be radiopaque such as, but not limited to, lead, tantalum, tungsten, gold, stainless steel or the like. Alternatively, the indicia may be a radiopaque polymer; such polymers are available under the trade name LATIGRAY from LATI Industries Thermoplasici S.p.A. of Italy, and may be directly adhered or molded into the outrigger.

By way of example only, while placing bone screws through a pedicle 42 (which is a small generally tubular structure connecting posterior elements of a vertebra 44 to the vertebral body), it is critical to ensure the screw is contained within the pedicle and does not breach the outer pedicle wall. Since the pedicle 42 is surrounded by delicate nervous tissue, a breach can have serious consequences for the patient, ranging from mild pain to paralysis. One way to mitigate the risk of a pedicle breach during screw placement (including preparation for screw placement, such as pilot hole formation and tapping) is to determine the angular orientation of the pedicle, and thereafter advance the necessary instruments and screws along the determined trajectory. By orienting the surgical access components along the pedicle trajectory, the surgical instruments and pedicle screws may be simply and efficiently advanced along the same trajectory, and thus avoid a breach by "eyeballing" alignment with the access components.

Thus, in spinal surgery, before a pilot hole is formed with the Jamshidi needle 40, the desired angular trajectory must first be determined. Preoperative superior view utilizing AP fluoroscopy, MRI or CAT scan imaging device(s) 20 can be used to determine the trajectory once the Jamshidi needle 40, in combination with the outrigger 10, has been placed at the anatomical site for which the surgery is to be conducted. C-arm fluoroscopes can be used extensively during many surgical procedures, for example. During spinal surgery for example, the C-arm can be used frequently to help locate specific structures of the spine, to direct the positioning of surgical instruments and/or instrumentation, and to verify the proper alignment and height of vertebra, among other uses. Imaging devices, such as the C-arm, are typically provided with a scale (not shown) indicating the orientation of the radiography beam 24 with respect to the patient and thus, in this example, the Jamshidi needle 40 in combination with the outrigger 10. In this manner, the imaging device 20 can direct a radiography beam 24 across the outrigger 10 at a known angle, causing the indicia 18 to become visible in the resulting image 20 (FIG. 2). As shown in FIG. 2, the indicia 18, e.g. front sight 30 can be viewed in combination with the rear sight 32 to define the outer boundaries of the desired angle, which is visible between the front sights 30. Spacing between the front sights 30 can be altered to provide any desired range of angle indication. It should also be noted that while only two front sights 30 are illustrated, any number of reference trajectory sights 34 may be provided to indicate angles or portions of angles without departing from the scope of the invention. In this manner, for surgical procedures such as those to the spine wherein the coronal (medial) angle (shown as indicia 26 on FIG. 6) increases approximately 5 degrees per level, with respect to centerline 28 from LI to the sacrum, a plurality of front sights 30 or reference trajectory sights 34 may be provided, whereby the surgeon can utilize a different front sight 30 or reference trajectory sight 34 for each level of the spine. In some embodiments, the front sights 30, rear sight(s) 32 and reference trajectory sights 34 may include different shapes including, but not limited to, numbers, letters, 2D and 3D geometric shapes and the like to indicate different angles, sights or reference sights. The indicia 18 may or may not be visible to the naked eye as the outrigger 10 is viewed. It should also be noted that while the present disclosure depicts a Jamshidi needle, the teachings of the present disclosure may be applied to other types of surgical tools without departing from the scope of the invention. For example, drills, saws, reamers, shapers and other hand-operated tools used for surgical operations may benefit from the teachings of the present invention. In addition, the teachings of the present invention may be utilized for the implantation of various implants, catheters, scopes and the like without departing from the scope of the invention. It should be further noted that while the trajectory guidance device, such as the outrigger 10 of the present embodiment, is illustrated as being attached to the surgical tool, the teachings of the present device include that the trajectory guidance device may also be utilized as a permanently secured or integrally formed portion of a surgical tool without departing from the scope of the invention.

Referring to FIGS. 1 and 3, one embodiment of an outrigger 10 is illustrated. In this embodiment, the radiolucent body portion 14 of the outrigger is provided with a guidance portion, such as a tube portion 50, for attachment to a structural portion of a surgical tool such as a Jamshidi needle 40. The tube portion 50 includes an inner lumen 52 sized to extend around the shaft 46. Thumb screws 54, friction or the like may be utilized to hold the outrigger in place on the shaft 46 or any other portion of a surgical tool that is generally round in shape. This construction also permits the outrigger 10 to be rotated as needed about the surgical tool and additional radiography shots taken in different planes whereby compound angles and the like may be indicated by the device.

Figure 4:
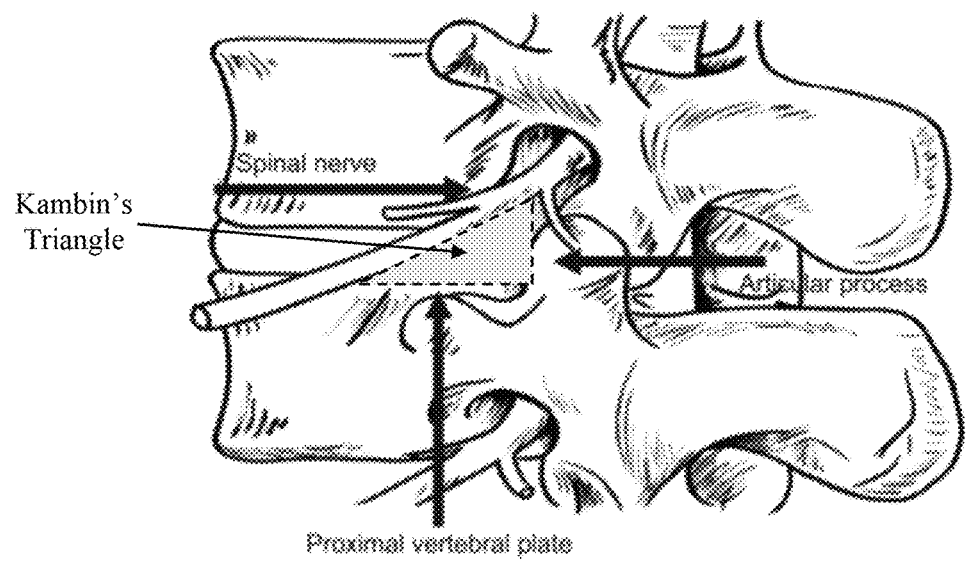
FIG. 4 is a representative illustration of a portion of a human spine, illustrating in particular the location of Kambin's Triangle, according to some embodiments.

For example, one embodiment of the disclosure includes a method of using the rotatable outrigger 10 to safely and reproducibly determine the appropriate angle for accessing an intervertebral disc space through Kambin's Triangle, described herein with combined reference to FIGS. 1-11. Referring first to FIG. 4, Kambin's Triangle refers to a right triangular-shaped area adjacent two vertebral bodies defined by the superior border of the caudal vertebral body (e.g. base), the dura/traversing nerve root (e.g. height), and the exiting spinal nerve root (e.g. hypotenuse). Accessing the disc space through this approach angle has several advantages, including minimizing damage to surrounding tissue and avoiding ligaments.

The first step in the example method is to deliver a surgical guidance instrument, for example the trajectory guidance instrument 100 described above (e.g. a Jamshidi needle 40 with attached outrigger 10), to a target pedicle on a patient in the manner described above in relation to FIGS. 1-2. For the purpose of illustration, the trajectory guidance instrument 100 is placed at an angle of 20° from center, however it should be understood that the trajectory guidance instrument 100 may be placed initially at any angle that is suitable and desirable to achieve the user's goals.

It should be appreciated that the trajectory guidance instrument can be calibrated to provide any desired angle. In some embodiments, the trajectory guidance instrument can provide angles of about 1°, about 5°, about 10°, about 15°, about 20°, about 25°, about 30°, about 35°, about 40°, about 45°, about 50°, about 55°, about 60°, about 65°, about 70°, about 75°, about 80°, about 85°, about 90°, or any amount or range therein in increments of 1°. In fact, the trajectory guidance instrument can include any desired gradations on the device for ease of reference during a surgical procedure as an angle scale portion as shown, for example, at FIGS. 2 and 3, and such gradations can include any of the angles listed herein, or even smaller gradations down to 0.1°.

Figure 5A:
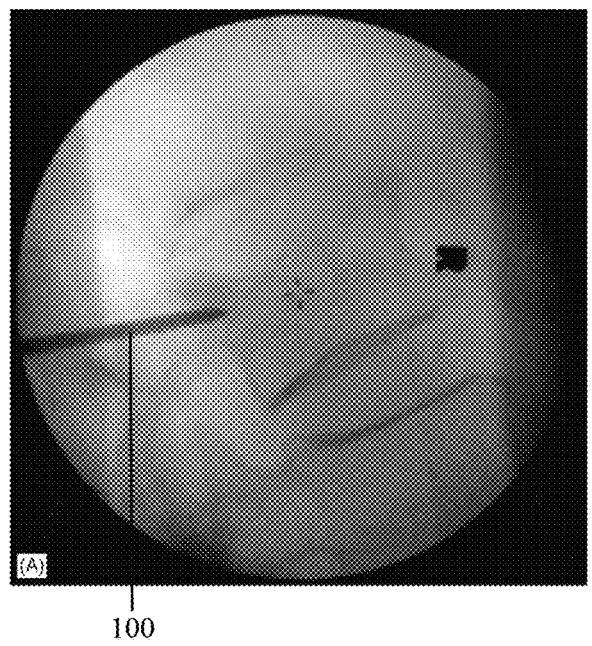
FIGS. 5A and 5B are radiographic images illustrating operation, according to some embodiments.
Figure 5B:
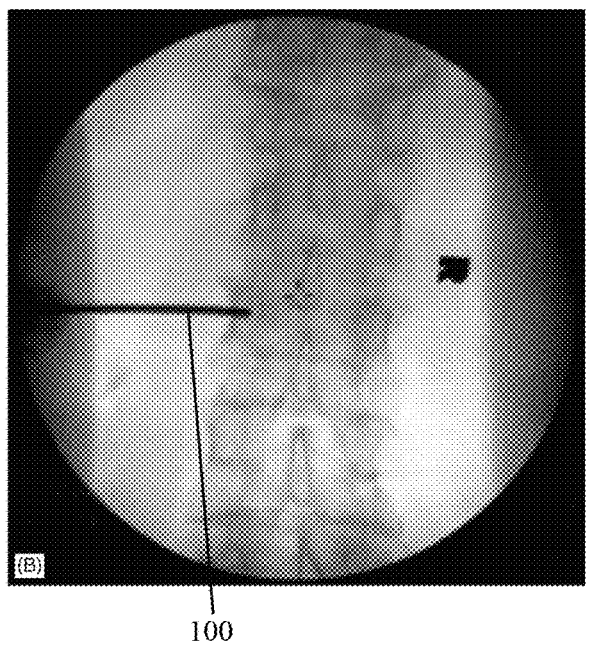

Referring to FIGS. 5A and 5B, the next step is to verify that the approach instrument (e.g. trajectory guidance instrument 100) is at the proper depth within the pedicle to correlate the desired depth for optimal Kambin's trajectory. This is accomplished using the C-arm fluoroscope described above, for example.

Figure 6:
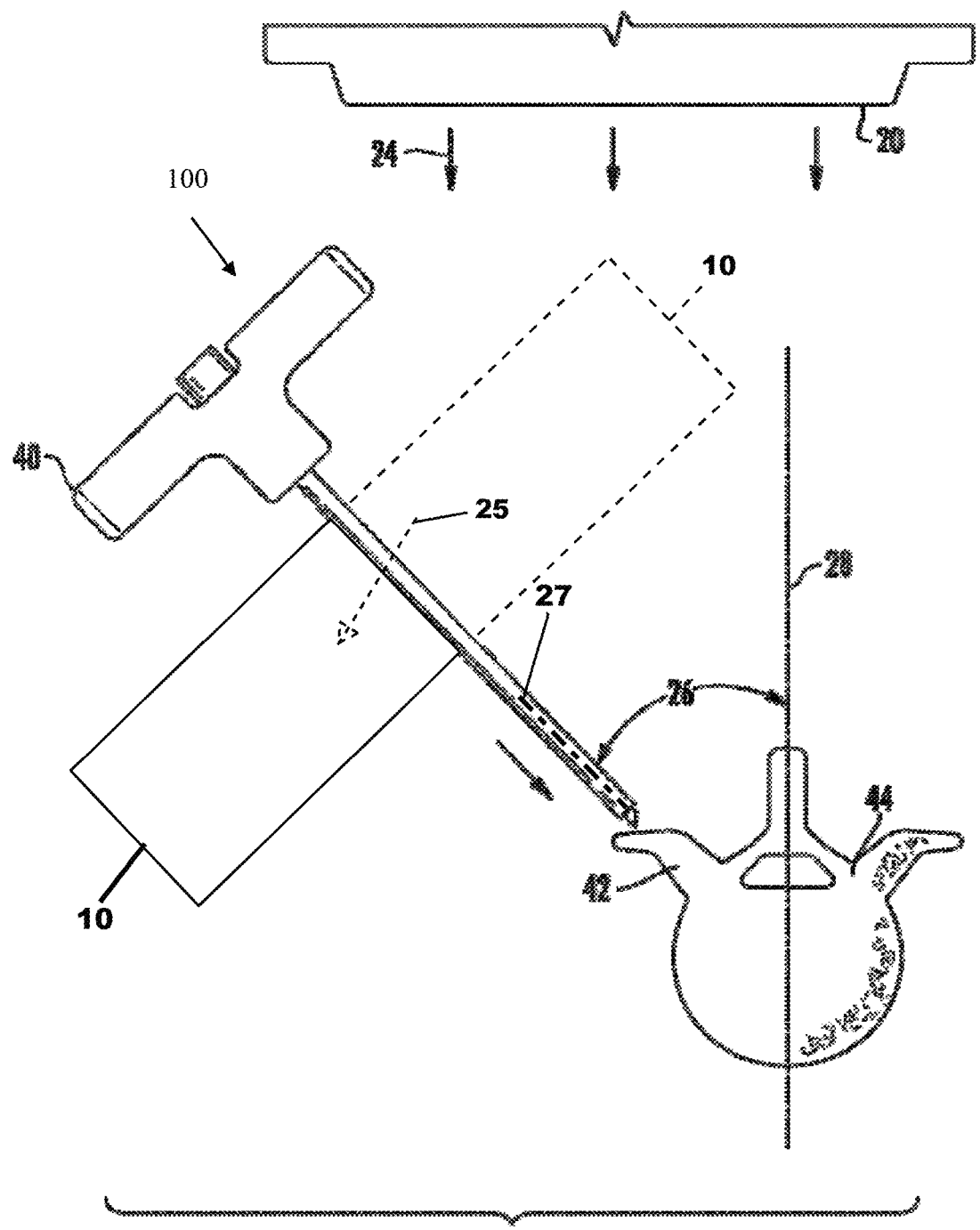
FIG. 6 is a side view of the trajectory guidance instrument of FIG. 1 with the outrigger repositioned, according to one example, according to some embodiments.

Referring to FIG. 6, the next step is to reposition 25 the orientation of the outrigger 10, a full 180° relative to the first surgical device or reference device, such as the Jamshidi needle 40, the central axis 27 of the implanted portion of the reference device forming a reference point of origin from which to measure a trajectory angle of the central axis of the implanted portion, or access portion, of a second surgical device (not shown). By way of example, this may include a step of rotating 25 the outrigger 10 about the Jamshidi needle 40 (e.g. for instances in which the outrigger is of the type described with respect to FIG. 3), however, in other embodiments, the outrigger 10 may need to be adjusted accordingly, to measure the trajectory angle of the central axis of the access portion of the second surgical device from the reference point of origin. This step of repositioning 25 the outrigger 10 relative to the Jamshidi needle 40 (the position of which remains unaltered) is necessary to achieve the approximately 45° approach angle required to enter the disc space through Kambin's Triangle. At this point, the angle of the Jamshidi needle 40 relative to the pedicle is known by way of completion of the process of placing the Jamshidi needle 40 described above. Since the angle needed to approach a disc space through Kambin's Triangle is known to be approximately 45°, the additional angle needed for the second approach instrument (to be advanced through Kambin's Triangle, but not shown) may be calculated by subtracting the placement angle of the Jamshidi needle 40 from the required Kambin's approach angle. Thus in the instant example, 45° (required Kambin's approach angle) minus 20° (angle of the Jamshidi needle placement) equal 25° (required additional angle of second approach angle relative to the Jamshidi needle 40).

Figure 7:
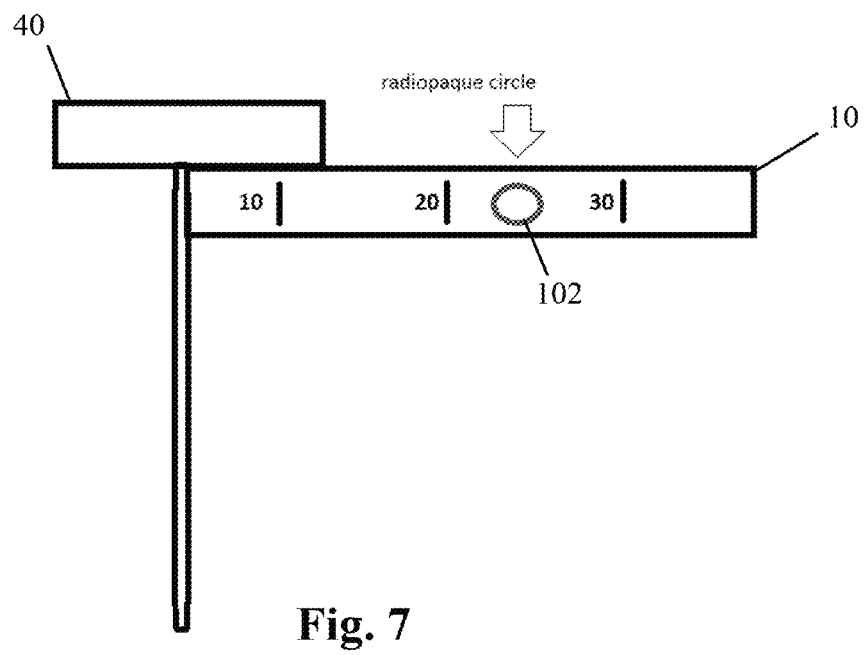
FIG. 7 is a side view of one example of a trajectory guidance instrument, according to some embodiments.
Figure 8:
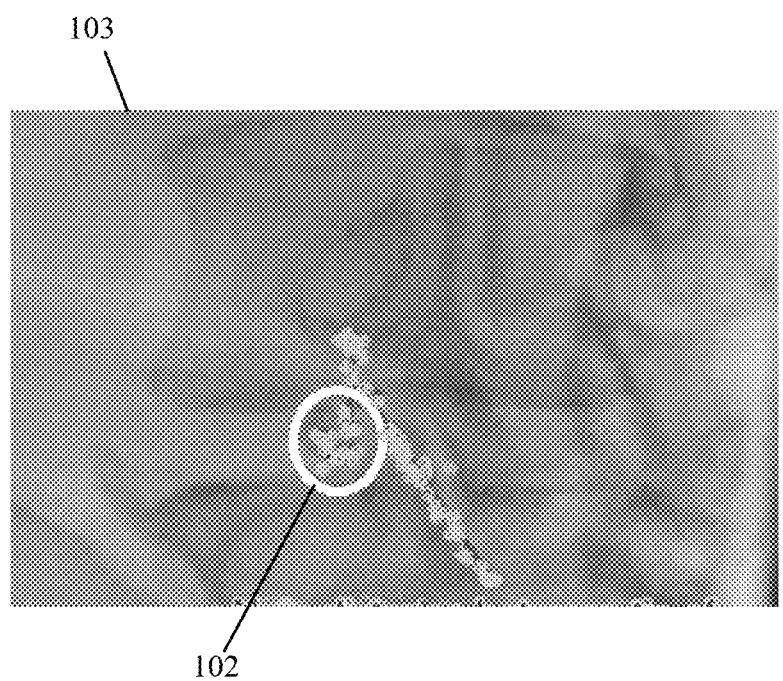
FIG. 8 is a radiographic image illustrating operation of the trajectory guidance instrument of FIG. 7, according to some embodiments.

Referring to FIG. 7, the outrigger 10 may include a secondary approach indicia 102 at the 25° mark to ensure proper alignment of the rotated 27 outrigger 10 and to verify the correct angle for entry of the second surgical device through Kambin's Triangle. By way of example, the secondary approach indicia 102 is depicted as a radiopaque circle, however any suitable radiopaque indicia may be used to verify the proper angle has been achieved from the reference point of origin. As with placement of the Jamshidi needle 40 described above, the imaging device 20 can direct a radiography beam 24 across the outrigger 10 at a known angle, causing the secondary approach indicia 102 to become visible in the resulting image 103 (FIG. 8). As shown in FIG. 8, the secondary indicia 102 can be viewed under fluoroscopy to ensure proper positioning of the second surgical device relative to the disc space and Kambin's Triangle. It should also be noted that while only one secondary indicator 102 is illustrated (at the 25° mark), any number of secondary indicia 102 may be provided to indicate angles or portions of angles without departing from the scope of the disclosure.

Figure 9:
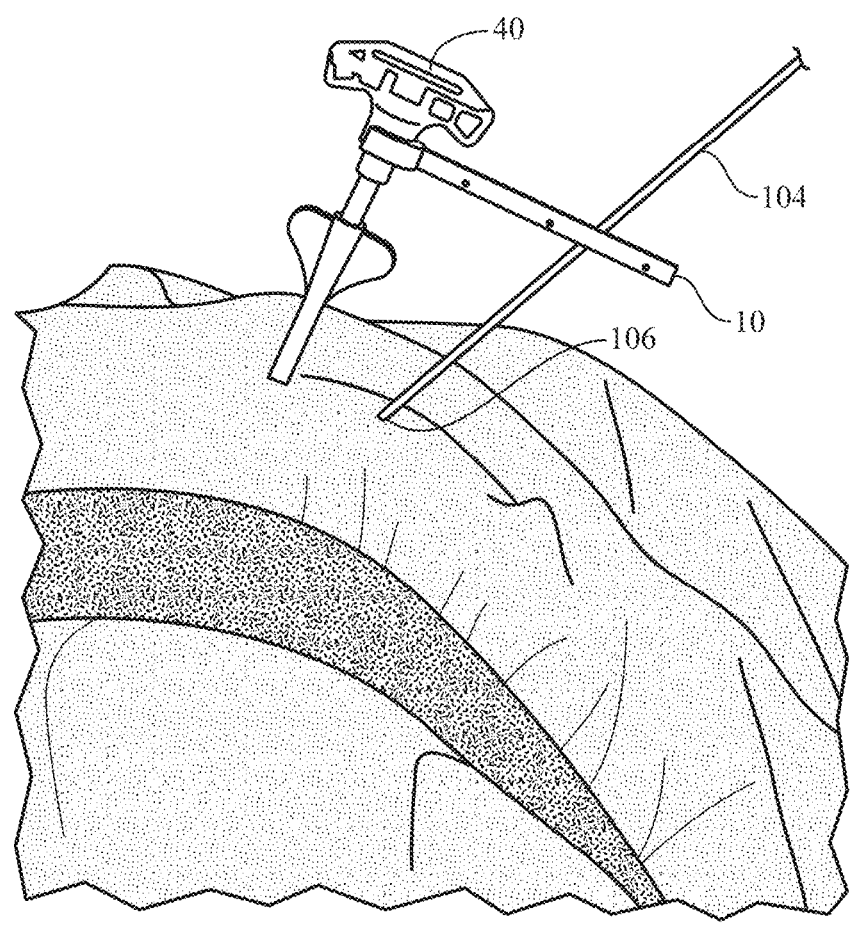
FIG. 9 is a perspective view of the trajectory guidance instrument of FIG. 7 in use with an example secondary approach instrument, according to some embodiments.
Figure 10:
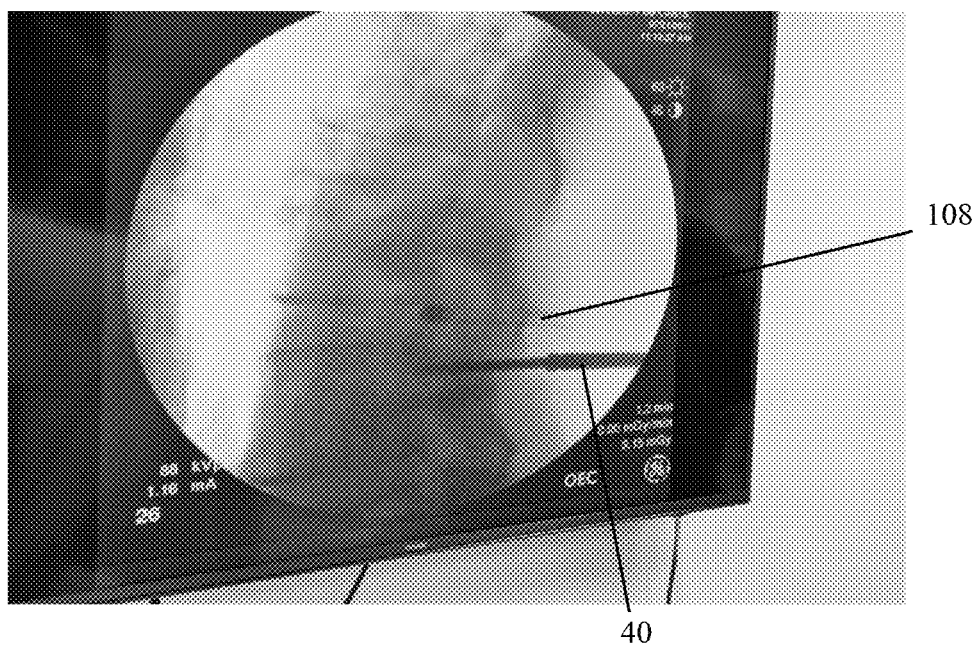
FIG. 10 is a radiographic image illustrating one step in the method, according to some embodiments; and, FIG. 11 is a representative illustration of a portion of a human spine, illustrating the relative position of the trajectory guidance instrument of FIG. 1 and a second approach instrument, according to some embodiments.
Figure 11:
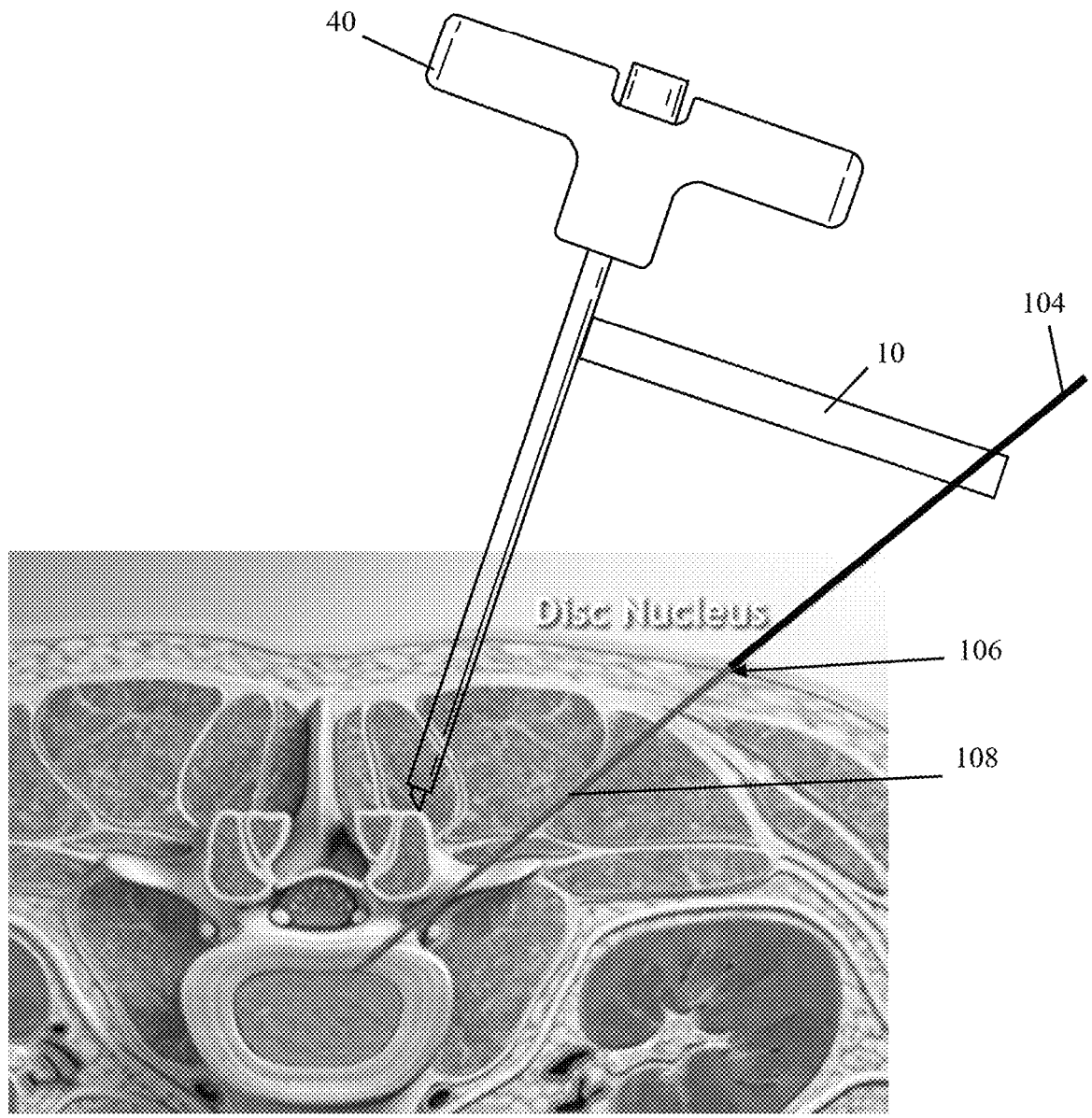

Referring to FIG. 9, the next step is to secure the Kambin's approach angle of the second surgical device. By way of example, this may be done by positioning a tube or cannula 104 such that the tube passes through the circle and the distal end of the tube 104 is touching the patient's skin at the point of entry 106. Once the tube is properly aligned, an incision may be made in the patient's skin at the point of entry (e.g. where the tube touches the skin). The second approach instrument 108, the second surgical device, may then be advanced through the cannula 104 (and incision) until it is about to reach the target disc. An x-ray image may be used at this point (FIG. 10) to ensure proper trajectory and to make any adjustments if necessary. Once the proper positioning of the second approach instrument 108 has been verified, the access portion of the second approach instrument may be pushed into the disc (FIG. 11).

At this point, the approach into the disc space through Kambin's Triangle has been established, and the desired procedure may continue. For example, this may include expansion of the surgical corridor (e.g. via sequential dilation), removing disc material, inserting intervertebral implants, and the like.

I claim:

1. A method of setting a surgical trajectory for access by a second surgical device using a fixed angle of a first surgical device in a subject, the method comprising:

obtaining a trajectory guidance device for a first surgical device and a second surgical device, the first surgical device and the second surgical device each having an access portion with a tip and a central axis concentric with the tip, the trajectory device having
 a guidance portion with a first rotatable axis concentric, or near concentric, with the central axis of the access portion of the first surgical device when in operable connection with the first surgical device; and,
 an angle scale portion;
 wherein, the trajectory guidance device is adapted for attaching to the first surgical device;

placing the guidance portion of the trajectory guidance device in operable connection with the first surgical device;

obtaining a radiograph of a target site within the subject using a source of radiation having a central beam, the central beam having an axis, and the radiograph having a center, the target site centered at or near the center of the radiograph, the obtaining including directing the axis of the central beam of a source of radiation for the radiograph at or near the center of the target site;

establishing a start position of the first surgical device on the subject, the establishing including
 placing the tip of the access portion of the first surgical device on the subject at a first point of entry for a first access that is at or near the center of the radiograph; and,
 orienting the central axis of the access portion of the first surgical device concentric or near concentric with the central beam of the source of radiation as a starting position for the first surgical device on the angle scale portion;

establishing a first direction of angulation and a first angle of the first access into the subject, the establishing including
 selecting the first direction of angulation and the first angle for a first pivoting the central axis of the access portion relative to the central axis of the central beam;
 aligning the angle scale with the first direction of angulation for the first pivoting; and,
 while immobilizing the tip of the access portion of the first surgical device at the first point of entry, performing the first pivoting of the central axis of the access portion of the first surgical device in the first direction of angulation until the first angle for the first pivoting is reached on the angle scale;

fixing the first surgical device at the first angle, the fixing including initiating the first access into the subject at the first point of entry and penetrating the tip of the first surgical device to a first depth into the subject that corresponds to a calibration of the first angle on the angle scale;

establishing a second direction of angulation and a second angle of a second access into the subject, the second direction of angulation and the second angle originating from tip of the first surgical device, and the establishing including
 selecting the second direction of angulation and the second angle for a second pivoting of the central axis of the access portion of the second surgical device relative to the central axis of the access portion of the first surgical device;
 aligning the angle scale with the second direction of angulation; and,
 while immobilizing the tip of the access portion of the second surgical device at a second point of entry, performing the second pivoting of the central axis of the access portion of the second surgical device in the second direction until the second angle is reached on the angle scale; and, fixing the second surgical device at the second angle, the fixing including initiating the second access into the subject at the second point of entry and penetrating the tip of the second surgical device to a second depth into the subject that corresponds to a calibration of the second angle on the angle scale.

2. The method of claim 1, wherein the target site is a vertebral pedicle, the first access of the first surgical device is into the vertebral pedicle of the subject, and the second access of the second surgical device is into a Kambin's Triangle adjacent to the vertebral pedicle.

3. The method of claim 1, wherein the first surgical device is a pin, a needle, a rod, a screw, or a combination thereof.

4. The method of claim 1, wherein the first surgical device is a trephine.

5. The method of claim 1, wherein the first surgical device is a trephine, and the second surgical device is a cutting instrument.

6. The method of claim 1, wherein the second surgical device is a dilator.

7. The method of claim 1, wherein the second surgical device is a catheter.

8. The method of claim 1, wherein the trajectory guidance device includes a secondary approach indicia for placement of the second surgical device.

9. The method of claim 1, wherein the trajectory guidance device rotates around the access portion of the first surgical device for fixing the second surgical device at the second angle.

10. A method of setting a trajectory angle for access by a second surgical device into a subject by referencing a first surgical device as a reference surgical device, the method comprising:
    implanting a portion of the reference surgical device in the subject to set a reference trajectory angle, wherein the reference trajectory angle is formed by the central axis of the implanted portion of the reference surgical device; and,
    establishing the trajectory angle for access by the second surgical device using the central axis of the implanted portion of the reference surgical device as a reference point of origin, the second surgical device having an access portion with a tip and a central axis, the trajectory angle having a second direction of angulation and a second angle of the central axis of the second surgical device, the trajectory angle originating from the tip of the first surgical device, the establishing including
        immobilizing the tip of the access portion of the second surgical device at a second point of entry into the subject, performing a second pivoting of the central axis of the access portion of the second surgical device in the second direction of angulation until the second angle is reached; and,
        measuring the trajectory angle of the central axis of access portion of the second surgical device from the reference point of origin with an angle scale portion on an angle measurement component.

11. The method of claim 10, wherein the measuring includes obtaining a trajectory guidance device operable for attaching to the reference surgical device.

12. The method of claim 10, wherein the reference surgical device has an implanted portion and a structural portion having a central axis, and the measuring includes
    obtaining a trajectory guidance device adapted for attaching to the structural portion of the reference surgical device and having
        a guidance portion with a first rotatable axis concentric, or near concentric, with the central axis of the structural portion of the reference surgical device when attached; and,
        an angle scale portion for determining the trajectory angle for access by the second surgical device.

13. The method of claim 10, wherein the reference surgical device is a pin, a needle, a rod, a screw, or a combination thereof.

14. The method of claim 10, wherein the reference surgical device is a trephine.

15. The method of claim 10, wherein the reference surgical device is a trephine, and the second surgical device is a cutting instrument.

16. The method of claim 10, wherein the second surgical device is a dilator.

17. The method of claim 10, wherein the second surgical device is a catheter.

18. The method of claim 10, wherein the reference surgical device is implanted into a vertebral pedicle at the reference trajectory angle, and the trajectory angle for access by the second surgical device is established for access into the Kambin's Triangle adjacent to the vertebral pedicle.

19. A kit for performing a spinal surgery on a subject, the kit comprising:
    a first surgical device having (i) an access portion and (ii) a structural portion having a central axis;
    a second surgical device having an access portion with a central axis; and,
    a trajectory guidance device adapted for operably connecting with, and rotating about, the structural portion of the first surgical device, and having an angle measurement component with an angle scale portion to establish the trajectory of access into the subject by the access portion of the second surgical device, wherein the angle measurement component comprises a rotatable portion and the angle scale portion comprises a body comprising a front sight and a rear sight positioned more distally than the front sight relative to a longitudinal axis of the rotatable portion.

20. The kit of claim 19, wherein the first surgical device is a trephine, the second surgical device is a dilator, and the trajectory guidance device has
    a guidance portion with a first rotatable axis concentric, or near concentric, with the central axis of the structural portion of the first surgical device when attached; and,
    an angle scale portion for determining the trajectory angle of the access portion of the second device for the access into the subject.

21. The kit of claim 19, wherein the rotatable portion comprises a tube portion.

22. The kit of claim 19, wherein the body is radiolucent and the sights are radiopaque.

* * * * *

UNITED STATES PATENT AND TRADEMARK OFFICE
CERTIFICATE OF CORRECTION

| | |
|---|---|
| PATENT NO. | : 11,259,880 B1 |
| APPLICATION NO. | : 16/258529 |
| DATED | : March 1, 2022 |
| INVENTOR(S) | : Wyatt Geist |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 405 days.

Signed and Sealed this
Thirty-first Day of January, 2023

*Katherine Kelly Vidal*

Katherine Kelly Vidal
*Director of the United States Patent and Trademark Office*